United States Patent
Sathaye (10) Patent No.: US 7,392,086 B2
(45) Date of Patent: Jun. 24, 2008

(54) IMPLANTABLE CARDIAC DEVICE AND METHOD FOR REDUCED PHRENIC NERVE STIMULATION

(75) Inventor: Alok S. Sathaye, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 250 days.

(21) Appl. No.: 11/114,569

(22) Filed: Apr. 26, 2005

(65) Prior Publication Data

US 2006/0241711 A1   Oct. 26, 2006

(51) Int. Cl.
*A61N 1/37* (2006.01)
(52) U.S. Cl. ............................. 607/27; 600/510; 607/9
(58) Field of Classification Search .................. 607/9, 607/27
See application file for complete search history.

(56) References Cited

U.S. PATENT DOCUMENTS

| | | | |
|---|---|---|---|
| 4,573,481 A | 3/1986 | Bullara | |
| 5,203,348 A | 4/1993 | Dahl et al. | |
| 5,230,337 A | 7/1993 | Dahl et al. | |
| 5,301,677 A | 4/1994 | Hsung | |
| 5,360,442 A | 11/1994 | Dahl et al. | |
| 5,366,496 A | 11/1994 | Dahl et al. | |
| 5,372,606 A | 12/1994 | Lang et al. | |
| 5,391,200 A | 2/1995 | KenKnight et al. | |
| 5,397,342 A | 3/1995 | Heil, Jr. et al. | |
| 5,411,525 A | 5/1995 | Swanson et al. | |
| 5,468,254 A | 11/1995 | Hahn et al. | |
| 5,545,186 A | 8/1996 | Olson et al. | |
| 5,545,202 A | 8/1996 | Dahl et al. | |
| 5,591,216 A | 1/1997 | Testerman et al. | |
| 5,603,732 A | 2/1997 | Dahl et al. | |
| 5,634,938 A | 6/1997 | Swanson et al. | |
| 5,658,318 A | 8/1997 | Stroetmann et al. | |
| 5,674,254 A | 10/1997 | Van Krieken | |
| 5,697,956 A | 12/1997 | Bornzin | |
| 5,718,720 A | 2/1998 | Prutchi et al. | |
| 5,735,883 A | 4/1998 | Paul et al. | |

(Continued)

OTHER PUBLICATIONS

U.S. Appl. No. 11/890,668, filed Aug. 7, 2007, Sathaye et al.

(Continued)

*Primary Examiner*—Carl H. Layno
*Assistant Examiner*—Yun Haeng Lee
(74) *Attorney, Agent, or Firm*—Hollingsworth & Funk, LLC (57) ABSTRACT

Methods and devices for reducing phrenic nerve stimulation of cardiac pacing systems involve delivering a pacing pulse to a ventricle of a heart. A transthoracic impedance signal is sensed, and a deviation in the signal resulting from the pacing pulse may be used to determine phrenic nerve stimulation. Methods may further involve detecting the phrenic nerve stimulation from the pacing pulse by delivering two or more pacing pulse to the ventricle of the heart, and determining a temporal relationship. A pacing vector may be selected from the two or more vectors that effects cardiac capture and reduces the phrenic nerve stimulation. A pacing voltage and/ or pulse width may be selected that provides cardiac capture and reduces the phrenic nerve stimulation. In other embodiments, a pacing pulse width and a pacing voltage may be selected from a patient's strength-duration curve that effects cardiac capture and reduces the phrenic nerve stimulation.

19 Claims, 9 Drawing Sheets

U.S. PATENT DOCUMENTS

| | | |
|---|---|---|
| 5,855,593 A | 1/1999 | Olson et al. |
| 5,916,243 A | 6/1999 | KenKnight et al. |
| 6,141,581 A | 10/2000 | Olson et al. |
| 6,221,011 B1 | 4/2001 | Bardy |
| 6,259,947 B1 | 7/2001 | Olson et al. |
| 6,270,457 B1 | 8/2001 | Bardy |
| 6,277,072 B1 | 8/2001 | Bardy |
| 6,280,380 B1 | 8/2001 | Bardy |
| 6,312,378 B1 | 11/2001 | Bardy |
| 6,336,903 B1 | 1/2002 | Bardy |
| 6,358,203 B2 | 3/2002 | Bardy |
| 6,360,127 B1 | 3/2002 | Ding et al. |
| 6,363,281 B1 | 3/2002 | Zhu et al. |
| 6,368,284 B1 | 4/2002 | Bardy |
| 6,398,728 B1 | 6/2002 | Bardy |
| 6,434,428 B1 | 8/2002 | Sloman et al. |
| 6,438,410 B2 | 8/2002 | Hsu et al. |
| 6,487,443 B2 | 11/2002 | Olson et al. |
| 6,493,586 B1 * | 12/2002 | Stahmann et al. ............. 607/27 |
| 6,597,951 B2 | 7/2003 | Kramer et al. |
| 6,611,712 B2 | 8/2003 | Spinelli et al. |
| 6,615,089 B1 | 9/2003 | Russie et al. |
| 6,640,136 B1 | 10/2003 | Helland et al. |
| 6,708,058 B2 | 3/2004 | Kim et al. |
| 6,731,985 B2 | 5/2004 | Bradley et al. |
| 6,738,668 B1 | 5/2004 | Mouchawar et al. |
| 6,772,008 B2 | 8/2004 | Zhu et al. |
| 6,915,160 B2 | 7/2005 | Auricchio et al. |
| 6,978,178 B2 | 12/2005 | Sommer et al. |
| 7,031,773 B1 | 4/2006 | Levine et al. |
| 7,194,313 B2 | 3/2007 | Libbus |
| 7,233,821 B2 | 6/2007 | Hettrick et al. |
| 2002/0143264 A1 | 10/2002 | Ding et al. |
| 2003/0065365 A1 * | 4/2003 | Zhu et al. ..................... 607/17 |
| 2005/0060002 A1 * | 3/2005 | Zhu et al. ..................... 607/19 |

OTHER PUBLICATIONS

U.S. Appl. No. 10/955,393, filed Sep. 30, 2004, Freeberg.

U.S. Appl. No. 11/520,879, filed Apr. 14, 2006, Brooke et al.

\* cited by examiner

IMPLANTABLE CARDIAC DEVICE AND METHOD FOR REDUCED PHRENIC NERVE STIMULATION

FIELD OF THE INVENTION

The present invention relates generally to implantable medical devices and, more particularly, to devices and methods that reduce phrenic nerve stimulation from cardiac pacing systems.

BACKGROUND OF THE INVENTION

When functioning normally, the heart produces rhythmic contractions and is capable of pumping blood throughout the body. However, due to disease or injury, the heart rhythm may become irregular resulting in diminished pumping efficiency. Arrhythmia is a general term used to describe heart rhythm irregularities arising from a variety of physical conditions and disease processes. Cardiac rhythm management systems, such as implantable pacemakers and cardiac defibrillators, have been used as an effective treatment for patients with serious arrhythmias.

Cardiac rhythm management systems typically comprise circuitry to sense electrical signals from the heart and a pulse generator for delivering electrical stimulation pulses to the heart. Leads extending into the patient's heart are connected to electrodes that contact the myocardium for sensing the heart's electrical signals and for delivering stimulation pulses to the heart in accordance with various therapies for treating the arrhythmias.

Cardiac rhythm management systems operate to stimulate the heart tissue adjacent to the electrodes to produce a contraction of the tissue. Pacemakers are cardiac rhythm management systems that deliver a series of low energy pace pulses timed to assist the heart in producing a contractile rhythm that maintains cardiac pumping efficiency. Pace pulses may be intermittent or continuous, depending on the needs of the patient. There exist a number of categories of pacemaker devices, with various modes for sensing and pacing one or more heart chambers.

SUMMARY OF THE INVENTION

The present invention involves various methods and devices for reducing phrenic nerve stimulation of cardiac pacing systems. Methods of cardiac pacing, in accordance with the present invention, involve delivering a pacing pulse to one or multiple ventricles of a heart using one of a plurality of vectors. A transthoracic impedance signal is sensed, and a deviation in the transthoracic impedance signal may be detected following the delivery of the pacing pulse. The presence of phrenic nerve stimulation resulting from the pacing pulse may be detected based on the deviation in the transthoracic impedance signal.

Methods of cardiac pacing, in accordance with the present invention, may further involve detecting phrenic nerve stimulation from the pacing pulse by delivering two or more pacing pulse to the ventricle of the heart, and determining a temporal relationship between the transthoracic impedance signal and the two or more pacing pulses. A pacing vector may be selected from the two or more vectors that effects cardiac capture and reduces the phrenic nerve stimulation.

Embodiments of methods in accordance with the present invention involve selecting a pacing voltage and/or pulse width that provides for cardiac capture and reduces the phrenic nerve stimulation. The transthoracic impedance signal may be evaluated for an inspiration event within an evaluation window, such as a window defined by the pacing pulse and about 500 milliseconds following the pacing pulse. In other embodiments, a pacing pulse width and a pacing voltage may be selected from a patient's strength-duration curve that effects cardiac capture and reduces the phrenic nerve stimulation.

Other embodiments of methods in accordance with the present invention involve transmitting information associated with the sensed cardiac signal and the sensed transthoracic impedance signal to a patient-external device. Pacing signal information may be received from the patient-external device. The pacing pulse may be altered based on the received pacing signal information.

Further embodiments in accordance with the present invention are directed to medical devices having two or more electrodes electrically coupled to a heart. A pulse delivery circuit may be configured to deliver a pacing pulse to a heart using the electrodes. A transthoracic impedance sensor may be provided by the device and configured to sense a transthoracic impedance signal. A control circuit may be coupled to the sensing circuit and the transthoracic impedance sensor, the control circuit configured to determine the presence of phrenic nerve stimulation resulting from the pacing pulse based on a deviation in the transthoracic impedance signal.

Other embodiments of devices in accordance with the present invention have the control circuit configured to provide pacing pulse parameters to the pulse delivery circuit, reducing phrenic nerve stimulation while maintaining cardiac capture. The control circuit may be configured to determine one or more pacing pulse parameters that reduce phrenic nerve stimulation while maintaining cardiac capture. A signal processor may be provided in a patient-external device or system, the signal processor and the control circuit coupled to respective communication devices to facilitate wireless communication between the signal processor and the control circuit. For example, the signal processor may be provided in a network server system, and coupled to communication devices to facilitate wireless communication between the signal processor and the control circuit. The control circuit may further be configured to select a pacing vector that reduces the phrenic nerve stimulation while maintaining cardiac capture.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings, which form a part hereof, and in which is shown by way of illustration, various embodiments in which the invention may be practiced. It is to be understood that other embodiments may be utilized, and structural and functional changes may be made without departing from the scope of the present invention.

An implanted device according to the present invention may include one or more of the features, structures, methods, or combinations thereof described hereinbelow. For example, a cardiac monitor or a cardiac stimulator may be implemented to include one or more of the advantageous features and/or processes described below. It is intended that such a monitor, stimulator, or other implanted or partially implanted device need not include all of the features described herein, but may be implemented to include selected features that provide for unique structures and/or functionality. Such a device may be implemented to provide a variety of therapeutic or diagnostic functions.

A wide variety of implantable cardiac monitoring and/or stimulation devices may be configured to implement phrenic nerve stimulation avoidance methodologies of the present invention. A non-limiting, representative list of such devices includes cardiac monitors, pacemakers, cardiovertors, defibrillators, resynchronizers, and other cardiac monitoring and therapy delivery devices. These devices may be configured with a variety of electrode arrangements, including transvenous, endocardial, and epicardial electrodes (i.e., intrathoracic electrodes), and/or subcutaneous, non-intrathoracic electrodes, including can, header, and indifferent electrodes, and subcutaneous array or lead electrodes (i.e., non-intrathoracic electrodes).

Embodiments of the present invention may be implemented in the context of a wide variety of cardiac devices, such as those listed above, and are referred to herein generally as patient-internal medical devices (PIMD) for convenience. A PIMD implemented in accordance with the present invention may incorporate one or more of the electrode types identified above and/or combinations thereof.

When a pace pulse produces a contraction in the heart tissue, the electrical cardiac signal preceding the contraction is denoted the captured response (CR). The captured response may include an electrical signal, denoted the evoked response signal, associated with the heart contraction, along with a superimposed signal associated with residual post pace polarization at the electrode-tissue interface. The magnitude of the residual post pace polarization signal, or pacing artifact, may be affected by a variety of factors including lead polarization, after-potential from the pace pulse, lead impedance, patient impedance, pace pulse width, and pace pulse amplitude, for example.

A pace pulse must exceed a minimum energy value, or capture threshold, to produce a contraction. It is desirable for a pace pulse to have sufficient energy to stimulate capture of the heart without expending energy significantly in excess of the capture threshold. Thus, accurate determination of the capture threshold provides efficient pace energy management. If the pace pulse energy is too low, the pace pulses may not reliably produce a contractile response in the heart and may result in ineffective pacing. If the pace pulse energy is too high, the patient may experience discomfort and the battery life of the device will be shorter.

Capture detection allows the cardiac rhythm management system to adjust the energy level of pace pulses to correspond to the optimum energy expenditure that reliably produces a contraction. Further, capture detection allows the cardiac rhythm management system to initiate a back-up pulse at a higher energy level whenever a pace pulse does not produce a contraction.

Capture may be verified by detecting if a cardiac signal following a pace pulse indicates a captured response. However, the captured response must be discerned from other responses, including the superimposed residual post pace polarization without capture, intrinsic beats, and fusion/pseudofusion beats.

Bi-ventricular pacing provides therapy options for patients suffering from heart failure. However, new challenges have been presented by placement of the left-ventricular lead via the coronary sinus in bi-ventricular pacing systems. Due to the proximity of the coronary veins to the phrenic nerve, left ventricular pacing may result in phrenic nerve stimulation. Phrenic nerve stimulation from cardiac pacing may cause the patient to exhibit uncomfortable breathing patterns timed with the left-ventricular pace. Bi-ventricular pacing PIMDs may also incorporate transthoracic impedance sensors, which provide a signal that may be used to determine information about the patient's breathing.

A patient's inspiration is associated with increasing transthoracic impedance, and expiration is associated with decreasing transthoracic impedance. Abnormal breathing patterns are detectable using breathing information inferred from a transthoracic impedance signal. In accordance with the present invention, evaluation of the transthoracic impedance signal following ventricular stimulation may be used to determine if the ventricular stimulation resulted in phrenic nerve stimulation. For example, by evaluating the transthoracic impedance signal following a ventricular pacing to determine phrenic nerve stimulation, the PIMD, which typically includes an automatic capture verification feature, can select a pacing vector, pacing voltage, pacing pulse width, or other pacing parameters, to reduce phrenic nerve stimulation while effecting capture.

Phrenic nerve stimulation, resulting in diaphragm stimulation and rapid changes in the breathing pattern, may be detected by evaluating the transthoracic impedance signal. For example, the transthoracic impedance signal may be evaluated within a time window following pacing pulse delivery, such as a window defined between a pacing pulse and about 500 milliseconds after the pacing pulse. If the transthoracic impedance signal exhibits a breathing event associated with the pace pulse, it may be assumed that the pace pulse is causing the breathing event, implying phrenic nerve stimulation. An example of such a breathing event is inspiration and/or expiration corresponding to the timing of the pace pulse, and/or a change in inspiration and/or expiration superimposed over the normal breathing pattern, where the change corresponds with the pace pulse timing.

Mitigating phrenic nerve stimulation may be accomplished several ways in accordance with the present invention. In one embodiment, during a threshold test using a particular pacing vector, phrenic nerve stimulation may be sensed using the transthoracic impedance signal. The device may change pacing vectors after detecting phrenic nerve stimulation, and attempt to find a vector that minimizes the phrenic nerve stimulation to the pace pulses. For example, a PIMD may detect phrenic nerve stimulation when using a unipolar pace vector, and attempt pacing using an extended bipolar vector to mitigate the phrenic nerve stimulation. A threshold test may then be attempted with the extended bipolar vector to determine if it effects capture and reduces phrenic nerve stimulation.

A PIMD may perform threshold tests using all available vectors, and select the best vector in terms of both desirable energy levels and reduced phrenic nerve stimulation. A search for a useful pacing vector, pacing amplitude, pacing pulse width, or other pacing parameters may be activated in either a command mode or an ambulatory mode. In a command mode, a physician may enable the test during follow-up examinations, or during remote follow-up using an advanced patient management (APM) system, as will be described in more detail below.

In an ambulatory mode, upon detection of phrenic nerve stimulation, a PIMD may select pacing parameters, such as pacing vector, pacing level, or the like, while effecting capture, such as by using capture threshold testing. The PIMD may also send an alert to a patient-external device prompting re-programming or other action.

Figure 1A:
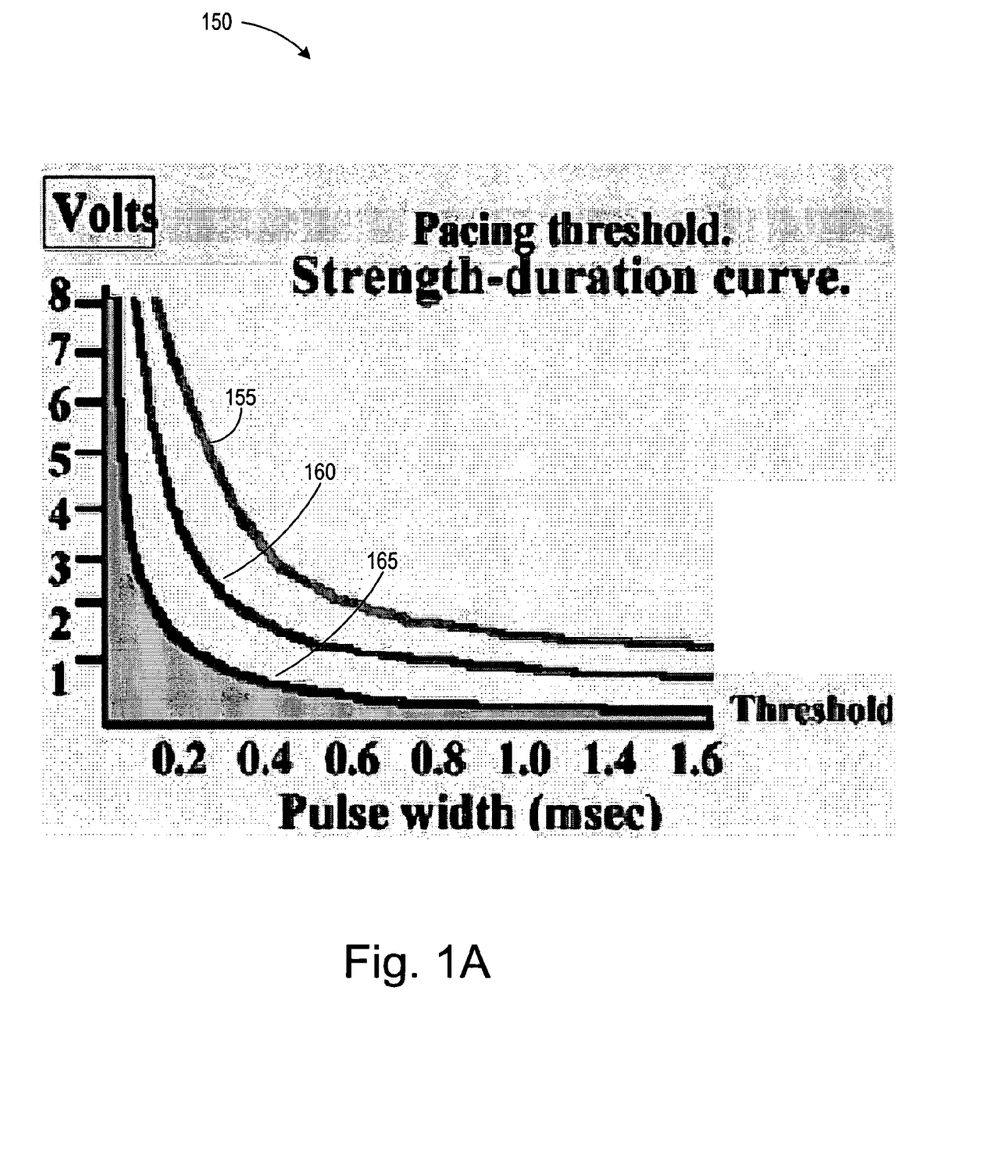
FIG. 1A is a graph illustrating examples of strength-duration curves.

In another embodiment in accordance with the present invention, a PIMD in ambulatory mode may incorporate automatic capture verification. The PIMD may incorporate the ability to determine a patient's strength-duration curve and/or use a programmed strength-duration curve to select one or more parameters. The PIMD, upon sensing phrenic nerve stimulation, may select another pacing voltage and pulse width on the patient's strength-duration curve that reduces or eliminates phrenic nerve stimulation. FIG. 1A is a graph 150 illustrating examples of strength-duration curves 155, 160, and 165. The graph 150 includes pulse voltage on the ordinate and pulse width on the abscissa. The curves 155, 160, and 165 may be used to select a combination of voltage and pulse width.

Other embodiments in accordance with the present invention provide PIMDs that automatically reduce phrenic nerve stimulation by selecting pacing vectors, pacing amplitudes, pacing pulse widths, or other pacing parameters when phrenic nerve stimulation is detected from a transthoracic impedance signal. This ensures that patients experience reduced breathing disruption and/or discomfort. Detection of phrenic nerve stimulation from the transthoracic impedance signal may be accomplished by determining an association between the pacing signal and a patients breathing inferred from the transthoracic impedance signal.

Figure 1B:
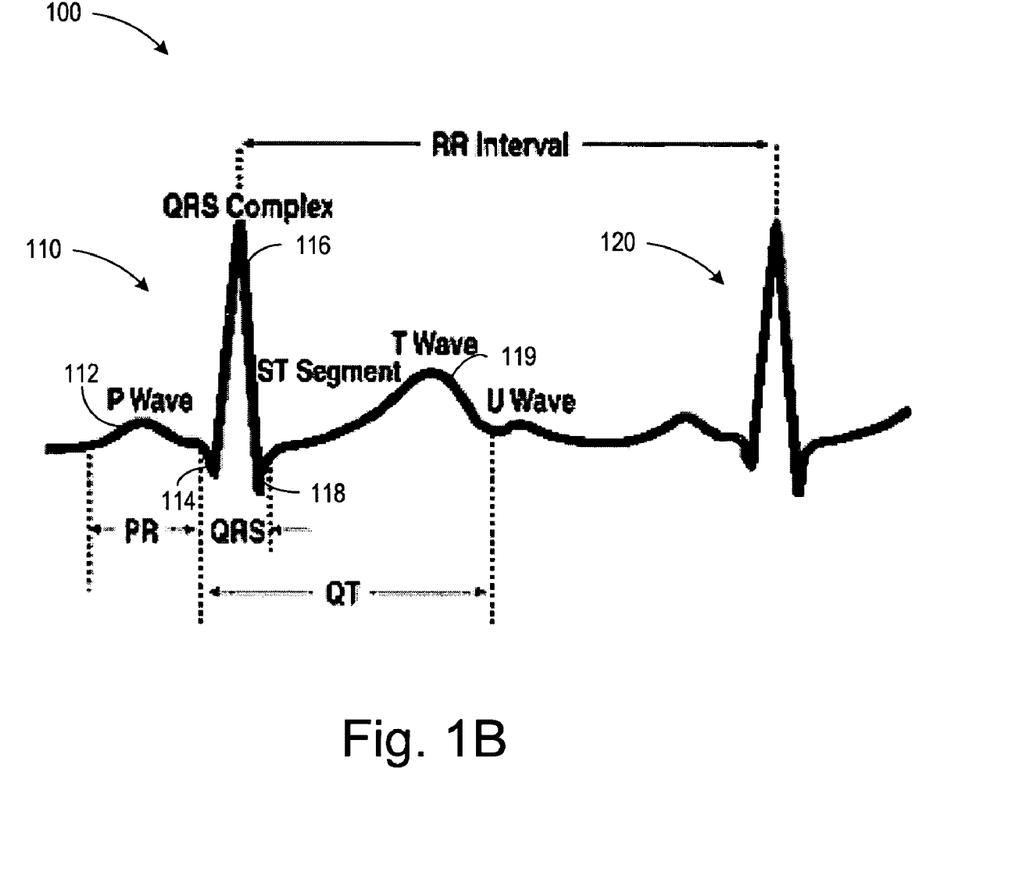
FIG. 1B is a pictorial diagram of an electrocardiogram for two consecutive heartbeats.

The relationship between a patients breathing, heartbeat (captured responses, non-captured responses, and intrinsic beats), and pacing may be determined using signals generated by and sensed using a PIMD. For example, an electrocardiogram (ECG) or electrogram (EGM) waveform describes the electrical activity of a patient's heart, where typically ECG refers to waveforms sensed from surface electrodes and EGM refers to waveforms sensed patient-internally. The graph in FIG. 1B illustrates an example of an EGM waveform 100 that describes the activation sequence of a patient's heart as recorded, for example, by a bi-polar cardiac sensing electrode. FIG. 1B is a magnified view of a first heartbeat 110, and a second heartbeat 120 of the EGM waveform 100. For purposes herein, the term heartbeat will be synonymous with cardiac cycle.

Referring to the first heartbeat 110, the portion of the EGM waveform representing depolarization of the atrial muscle fibers is referred to as a P-wave 112. Depolarization of the ventricular muscle fibers is collectively represented by a Q 114, R 116, and S 118 waves of the EGM waveform 100, typically referred to as the QRS complex, which is a well-known morphologic feature of electrocardiograms. Finally, the portion of the waveform representing repolarization of the ventricular muscle fibers is known as a T wave 119. Between contractions, the EGM waveform returns to an isopotential level.

In general, the quality of the electrocardiogram sensed from one pair of electrodes of a PIMD depends on the orientation of the electrodes with respect to the depolarization wavefront produced by the heart. The signal sensed on an electrode bi-pole is the projection of the EGM vector in the direction of the bi-pole. The sensed EGM waveform 100 illustrated in FIG. 1BA is typical of a far-field EGM signal, effectively a superposition of all the depolarizations occurring within the heart that result in contraction.

The EGM waveform 100 may also be obtained indirectly, such as by using a signal separation methodology. Signal separation methodologies, such as blind source separation (BSS), are able to separate signals from individual sources that are mixed together into a composite signal. The main principle of signal separation works on the premise that spatially distributed electrodes collect components of a signal from a common origin (e.g., the heart) with the result that these components may be strongly correlated to each other. In addition, these components may also be weakly correlated to components of another origin (e.g., noise).

A signal separation algorithm may be implemented to separate these components according to their sources and produce one or more cardiac signal vectors associated with all or a portion of one or more cardiac activation sequences based on the source separation. Cardiac activation sequence monitoring and/or tracking algorithms that exploit the strong correlation of signals from a common origin (the heart) across spatially distributed electrodes have been described further in commonly assigned U.S. patent application Ser. No. 10/955, 397 filed Sep. 30, 2004, which is hereby incorporated herein by reference. Phrenic nerve avoidance algorithms in accordance with the present invention may preferably select vectors that effect capture of a patient's heart while avoiding unwanted phrenic nerve stimulation.

Figure 2A:
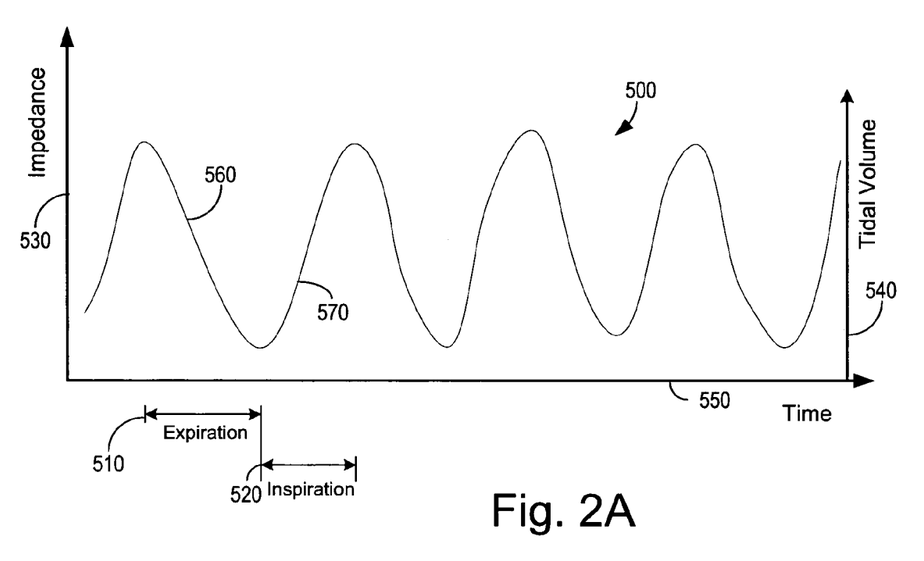
FIG. 2A is a graph of a normal respiration signal measured by a transthoracic impedance sensor that may be utilized for monitoring, diagnosis and/or therapy in accordance with embodiments of the invention.

A transthoracic impedance sensor provides another signal to the PIMD that may be analyzed to determine several events/features related to both breathing and other events. Referring now to FIG. 2A, an impedance signal 500 is illustrated. Transthoracic impedance is used in accordance with the present invention to detect phrenic nerve stimulation, and may also be useful for detecting sleep-state and other indirect measurements, such as seizures and breathing disorders. The impedance signal 500 may be developed, for example, from an impedance sense electrode in combination with an ITCS device. The impedance signal 500 is proportional to the transthoracic impedance, illustrated as an Impedance 530 on the abscissa of the left side of the graph in FIG. 2A.

The impedance 530 increases during any respiratory inspiration 520 and decreases during any respiratory expiration 510. The impedance signal 500 is also proportional to the amount of air inhaled, denoted by a tidal volume 540, illustrated on the abscissa of the right side of the graph in FIG. 2A. The variations in impedance during respiration, identifiable as the peak-to-peak variation of the impedance signal 500, may be used to determine the respiration tidal volume 540. Tidal volume 540 corresponds to the volume of air moved in a breath, one cycle of expiration 510 and inspiration 520. A minute ventilation may also be determined, corresponding to the amount of air moved per a minute of time 550 illustrated on the ordinate of the graph in FIG. 2A.

Figure 2B:
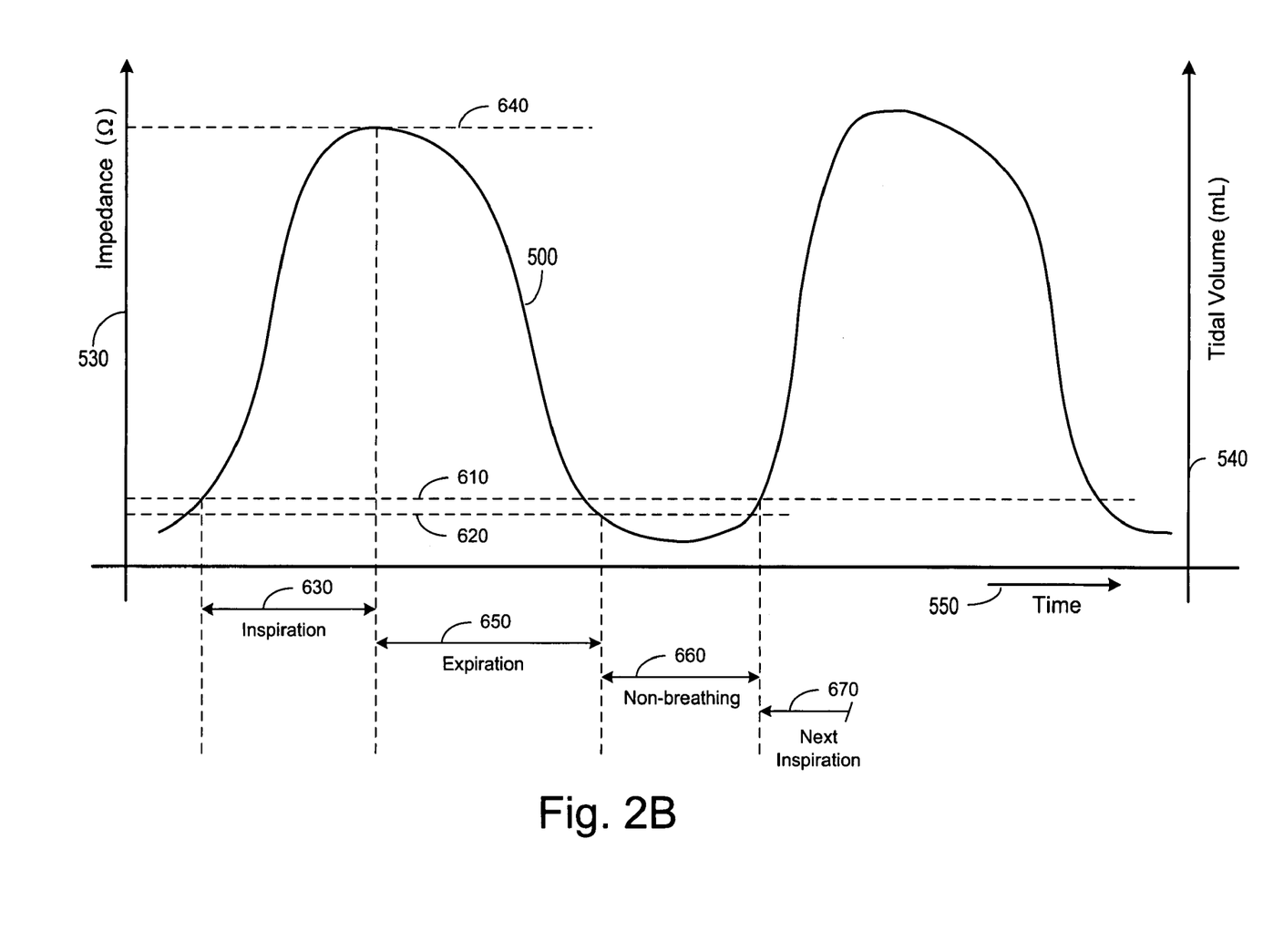
FIG. 2B is a respiration signal graph illustrating respiration intervals used for disordered breathing detection according to embodiments of the invention.
Figure 3:
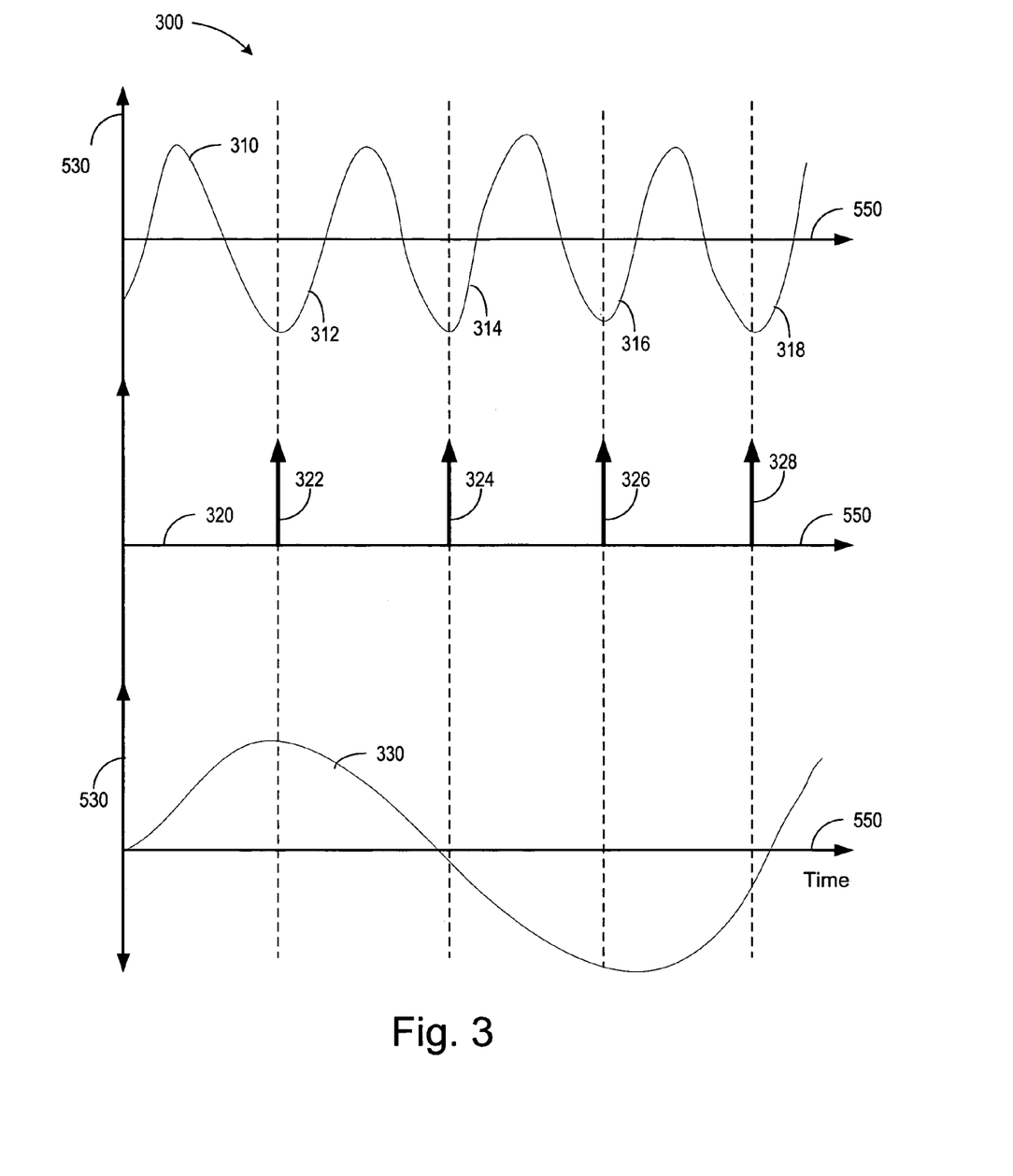
FIG. 3 is a transthoracic impedance graph illustrating detection of phrenic nerve stimulation in accordance with embodiments of the invention.

FIGS. 2A, 2B, and 3 are graphs of transthoracic impedance and tidal volume, similar to FIG. 2A previously described. As in FIG. 2A, FIGS. 2B and 3, illustrate the impedance signal 500 proportional to the transthoracic impedance, again illustrated as Impedance 530 on the abscissa of the left side of the graphs in FIGS. 2A, 2B, and 3. The impedance 530 increases during any respiratory inspiration 520 and decreases during any respiratory expiration 510. As before, the impedance signal 500 is also proportional to the amount of air inhaled, denoted the tidal volume 540, illustrated on the abscissa of the right side of the graph in FIGS. 2A, 2B, and 3. The magnitude of variations in impedance and tidal volume during respiration are identifiable as the peak-to-peak variation of the impedance signal 500.

FIG. 2B illustrates respiration intervals used for breathing detection useful in accordance with embodiments of the invention. Respiration intervals may be used to detect disordered breathing, as well as provide other sleep-state and breathing information. Detection of disordered breathing may involve defining and examining a number of respiratory cycle intervals. A respiration cycle is divided into an inspiration period corresponding to the patient inhaling, an expiration period, corresponding to the patient exhaling, and a non-breathing period occurring between inhaling and exhaling. Respiration intervals are established using an inspiration threshold 610 and an expiration threshold 620. The inspiration threshold 610 marks the beginning of an inspiration period 630 and is determined by the transthoracic impedance signal 500 rising above the inspiration threshold 610. The inspiration period 630 ends when the transthoracic impedance signal 500 is a maximum 640. The maximum transthoracic impedance signal 640 corresponds to both the end of the inspiration interval 630 and the beginning of an expiration interval 650. The expiration interval 650 continues until the transthoracic impedance 500 falls below an expiration threshold 620. A non-breathing interval 660 starts from the end of the expiration period 650 and continues until the beginning of a next inspiration period 670.

FIG. 3 is a graph 300 illustrating detection of phrenic nerve stimulation in accordance with embodiments of the invention. A transthoracic impedance signal 310 and a transthoracic impedance signal 330 are shown with respect to a cardiac pace signal 320. The cardiac pace signal 320 is illustrated as having a first pace 322, a second pace 324, a third pace 326, and a fourth pace 328. The paces 322, 324, 326 and 328 correspond to inspiration events 312, 314, 316, and 318 respectively of the transthoracic impedance signal 310. The paces 322, 324, 326 and 328 do not perceptively correspond to any features of the transthoracic impedance signal 330 in this illustration.

Although the inspiration events 312, 314, 316, and 318 are illustrated to correspond to inspiration events of complete breathing cycles for illustrative purposes, the paces 322, 324, 326 and 328 may correspond to other features of the transthoracic impedance signal 310. For example, the inspiration events 312, 314, 316, and 318 may correspond to expiration events of complete breathing cycles, or partial breathing events, such as spasms, superimposed on breathing cycles with periods that do not correspond to the pacing rate without departing from the scope of the present invention.

Figure 4:
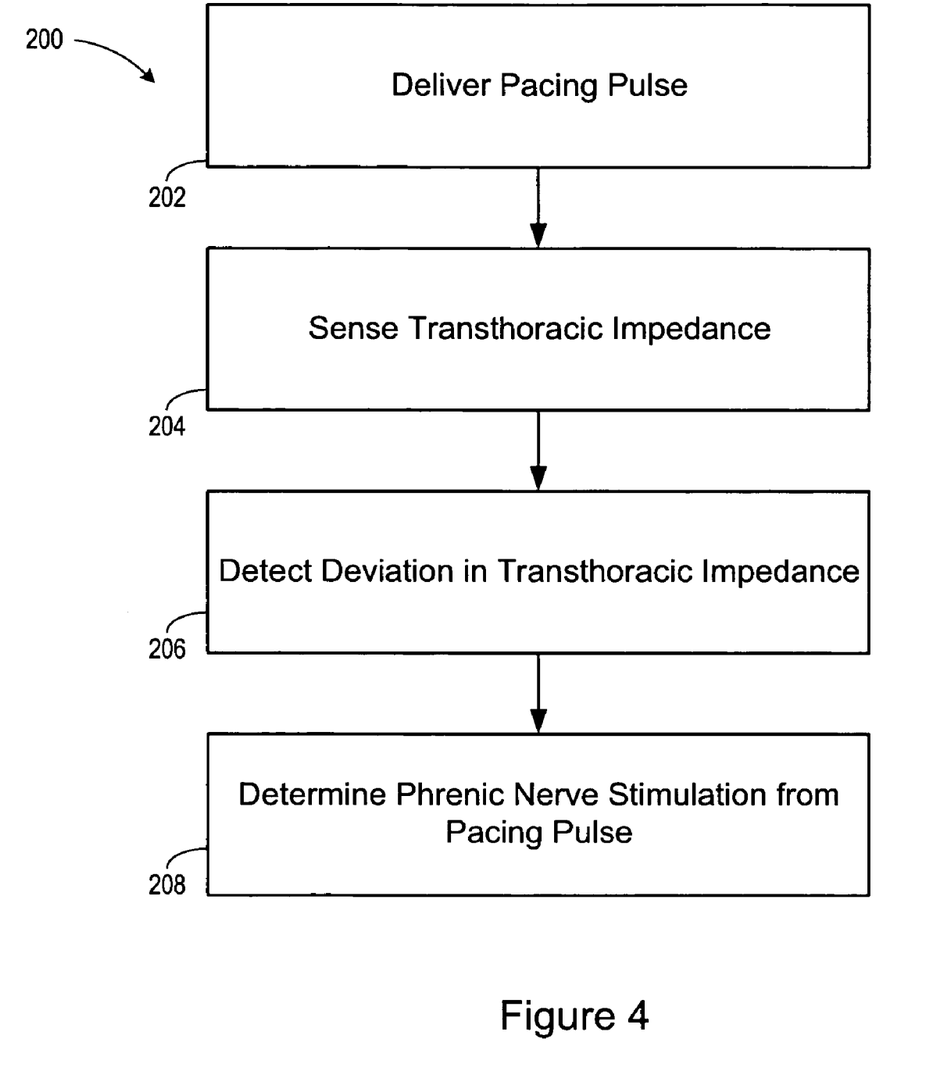
FIG. 4 is a flow chart of a method of reducing phrenic nerve stimulation in accordance with embodiments of the present invention.

FIG. 4 is a flow chart of a method 200 of determining phrenic nerve stimulation in accordance with embodiments of the present invention. Pacing pulses 200 are delivered to a patient's heart. A transthoracic impedance signal 204 is sensed. A deviation 206 of the transthoracic impedance signal 204 is detected that corresponds to the pacing pulses 202. Phrenic nerve stimulation 208 is determined from the deviation 206.

For example, pacing pulses 200 may be delivered to the patient's heart using a first vector, at a first pacing amplitude and rate. The transthoracic impedance signal 204 may exhibit the deviation 206 as a small spasm signal superimposed over the transthoracic impedance signal 204 variation due to breathing. The transthoracic impedance signal 204 may be filtered to detect the deviation 206, such as by using a bandpass filter centered at the first pacing rate.

If phrenic nerve stimulation 208 is detected, a PIMD in accordance with the present invention may alter one or more parameters to reduce the phrenic nerve stimulation. For example, the PIMD may change vectors searching for a vector that reduces the phrenic nerve stimulation. The PIMD may alter one or more of vector, amplitude, pulse width, or other parameter to reduce the phrenic nerve stimulation. It may be desirable to verify phrenic nerve stimulation for a given vector, such as by providing an extra pace during the cardiac refractory period, to determine phrenic nerve response to the extra pace independent of cardiac motion.

Figure 5:
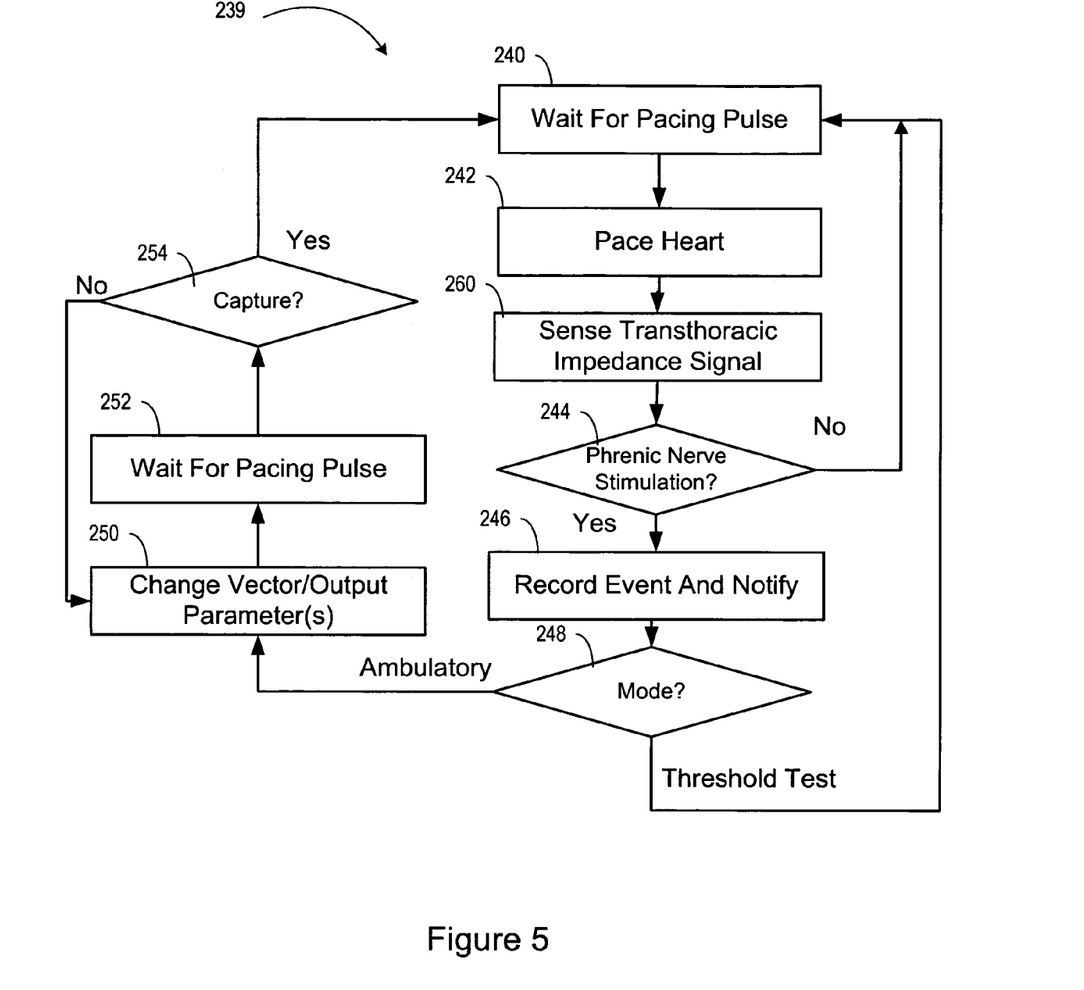
FIG. 5 is a flow chart of another method of reducing phrenic nerve stimulation in accordance with embodiments of the present invention.

FIG. 5 is a flow chart of another method 239 of reducing phrenic nerve stimulation in accordance with embodiments of the present invention. At block 242, the heart is paced at a predetermined rate and amplitude. Transthoracic impedance is sensed 260, and the transthoracic impedance signal is examined to determine if there is diaphragm movement responsive to the cardiac pace. For example, a deviation of the filtered transthoracic impedance signal above a predetermined threshold may be used to identify phrenic nerve stimulation 244. The transthoracic impedance signal may be examined within a time window following each pace pulse for an indication of phrenic stimulation. For example, a window that opens at the left-ventricular pace pulse timing and closes 500 milliseconds after the left-ventricular pace pulse timing may be used to examine the transthoracic impedance signal for a change indicative of phrenic nerve stimulation. In another embodiment, a lock-in amplifier may be used, where the pace signal and transthoracic impedance signal are analyzed for indications of phrenic nerve stimulation.

If no phrenic nerve stimulation is found, a wait 240 occurs until the next scheduled pace pulse. If phrenic nerve stimulation is found, the event 246 may be recorded and/or a notification may occur. For example, the controller of a PIMD may be notified that phrenic nerve stimulation is occurring, and the controller may enter into an optimization algorithm, such as in a command mode, that searches for new vectors, settings, or other controlled parameters that effect capture with a minimum of phrenic nerve stimulation. If a determination 248 is made that the optimization algorithm occurs or is in process by the controller, then the recorded event 246 information is used by the controller, and the method 239 proceeds to the wait 240 for the next pace pulse.

If the determination 248 finds that the PIMD is in ambulatory mode, the PIMD may change 250 a vector, and/or other output parameter(s), wait 252 for the next scheduled pace pulse, and determine 254 if capture occurs at the new setting. For example, the ambulatory mode may simply reduce the pace amplitude at the change 250, and verify that capture still occurs at the reduced level using the determination 254. In alternate embodiments for selecting parameters in ambulatory mode, parameters may be selected from a patient's strength-duration curve that effects cardiac capture and reduces the phrenic nerve stimulation. The PIMD may select pacing pulse width and pacing voltage parameters that lie on a patient's strength-duration curve, to find a set of parameters that reduces and/or minimizes phrenic nerve stimulation. If capture determination 254 is yes after selecting the new parameter(s), then the method 239 returns to the wait 240. If capture determination 254 is no, then another change 250 is made, and the change loop 250, 252, 254 is repeated until a new setting is found that effects capture, before the method 239 continues to the wait 240.

Figure 6:
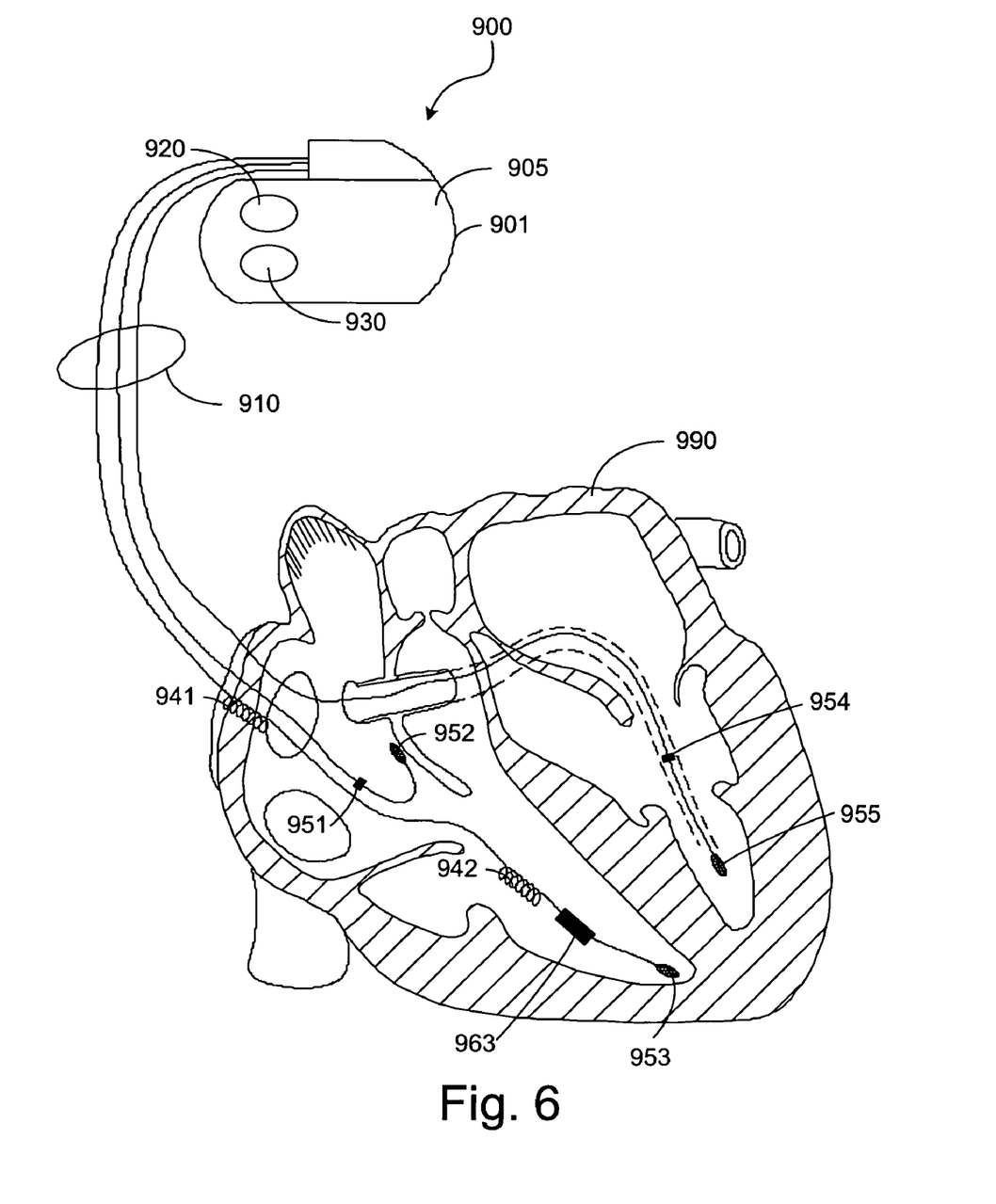
FIG. 6 is an illustration of an implantable cardiac device including a lead assembly shown implanted in a sectional view of a heart, in accordance with embodiments of the invention.

Referring now to FIG. 6, the implantable device illustrated in FIG. 6 is an embodiment of a PIMD implementing phrenic nerve stimulation avoidance methodologies in accordance with the present invention. In this example, the implantable device includes a cardiac rhythm management device (CRM) 900 including an implantable pulse generator 905 electrically and physically coupled to an intracardiac lead system 910.

Portions of the intracardiac lead system 910 are inserted into the patient's heart 990. The intracardiac lead system 910 includes one or more electrodes configured to sense electrical cardiac activity of the heart, deliver electrical stimulation to the heart, sense the patient's transthoracic impedance, and/or sense other physiological parameters, e.g., cardiac chamber pressure or temperature. Portions of the housing 901 of the pulse generator 905 may optionally serve as a can electrode.

Communications circuitry is disposed within the housing 901 for facilitating communication between the pulse generator 905 and an external communication device, such as a portable or bed-side communication station, patient-carried/worn communication station, or external programmer, for example. The communications circuitry may also facilitate unidirectional or bidirectional communication with one or more implanted, external, cutaneous, or subcutaneous physiologic or non-physiologic sensors, patient-input devices and/or information systems.

The pulse generator 905 may optionally incorporate a motion detector 920 that may be used to sense patient activity as well as various respiration and cardiac related conditions. For example, the motion detector 920 may be optionally configured to sense snoring, activity level, and/or chest wall movements associated with respiratory effort, for example. The motion detector 920 may be implemented as an accelerometer positioned in or on the housing 901 of the pulse generator 905. If the motion sensor is implemented as an accelerometer, the motion sensor may also provide respiratory, e.g. rales, coughing, and cardiac, e.g. S1-S4 heart sounds, murmurs, and other acoustic information. Accelerometers may also be used to detect phrenic nerve stimulation, which is further described in commonly owned U.S. Pat. No. 6,772,008, which is hereby incorporated herein by reference.

The lead system 910 and pulse generator 905 of the CRM 900 may incorporate one or more transthoracic impedance sensors that may be used to acquire the patient's respiration waveform, or other respiration-related information. The transthoracic impedance sensor may include, for example, one or more intracardiac electrodes 941, 942, 951-955, 963 positioned in one or more chambers of the heart 990. The intracardiac electrodes 941, 942, 951-955, 963 may be coupled to impedance drive/sense circuitry 930 positioned within the housing of the pulse generator 905.

In one implementation, impedance drive/sense circuitry 930 generates a current that flows through the tissue between an impedance drive electrode 951 and a can electrode on the housing 901 of the pulse generator 905. The voltage at an impedance sense electrode 952 relative to the can electrode changes as the patient's transthoracic impedance changes. The voltage signal developed between the impedance sense electrode 952 and the can electrode is detected by the impedance sense circuitry 930. Other locations and/or combinations of impedance sense and drive electrodes are also possible.

The lead system 910 may include one or more cardiac pace/sense electrodes 951-955 positioned in, on, or about one or more heart chambers for sensing electrical signals from the patient's heart 990 and/or delivering pacing pulses to the heart 990. The intracardiac sense/pace electrodes 951-955, such as those illustrated in FIG. 6, may be used to sense and/or pace one or more chambers of the heart, including the left ventricle, the right ventricle, the left atrium and/or the right atrium. The lead system 910 may include one or more defibrillation electrodes 941, 942 for delivering defibrillation/cardioversion shocks to the heart.

The pulse generator 905 may include circuitry for detecting cardiac arrhythmias and/or for controlling pacing or defibrillation therapy in the form of electrical stimulation pulses or shocks delivered to the heart through the lead system 910. The pulse generator 905 may also incorporate circuitry, structures and functionality of the implantable medical devices disclosed in commonly owned U.S. Pat. Nos. 5,203,348; 5,230,337; 5,360,442; 5,366,496; 5,397,342; 5,391,200; 5,545,202; 5,603,732; and 5,916,243; 6,360,127; 6,597,951; and US Patent Publication No. 2002/0143264, which are hereby incorporated herein by reference.

Figure 7:
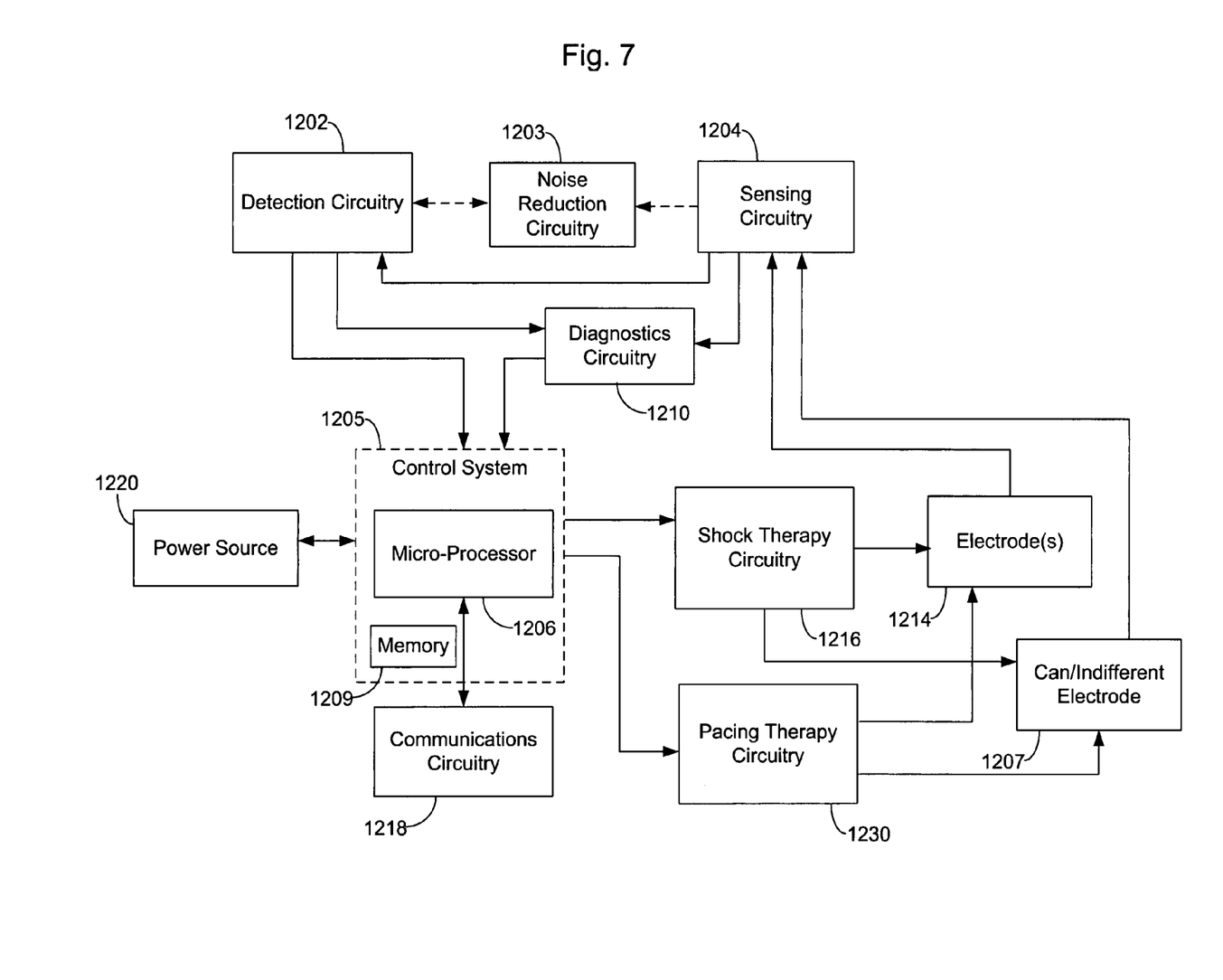
FIG. 7 is a block diagram illustrating various components of an implantable cardiac device in accordance with an embodiment of the present invention.

FIG. 7 is a block diagram depicting various componentry of different arrangements of a PIMD in accordance with embodiments of the present invention. The components, functionality, and configurations depicted in FIG. 7 are intended to provide an understanding of various features and combinations of features that may be incorporated in a PIMD. It is understood that a wide variety of device configurations are contemplated, ranging from relatively sophisticated to relatively simple designs. As such, particular PIMD configurations may include some componentry illustrated in FIG. 7, while excluding other componentry illustrated in FIG. 7.

Illustrated in FIG. 7 is a processor-based control system 1205 which includes a micro-processor 1206 coupled to appropriate memory (volatile and/or non-volatile) 1209, it being understood that any logic-based control architecture may be used. The control system 1205 and associated components provide pacing therapy to the heart. The electrical energy delivered by the PIMD may be in the form of low energy pacing pulses or may also include high-energy pulses for cardioversion or defibrillation.

Cardiac signals are sensed using the electrode(s) 1214 and the can or indifferent electrode 1207 provided on the PIMD housing. Cardiac signals may also be sensed using only the electrode(s) 1214, such as in a non-active can configuration. As such, unipolar, bipolar, or combined unipolar/bipolar electrode configurations as well as multi-element electrodes and combinations of noise canceling and standard electrodes may be employed. The sensed cardiac signals are received by sensing circuitry 1204, which includes sense amplification circuitry and may also include filtering circuitry and an analog-to-digital (A/D) converter. The sensed cardiac signals processed by the sensing circuitry 1204 may be received by noise reduction circuitry 1203, which may further reduce noise before signals are sent to the detection circuitry 1202.

Noise reduction circuitry 1203 may also be incorporated after sensing circuitry 1204 in cases where high power or computationally intensive noise reduction algorithms are required. The noise reduction circuitry 1203, by way of amplifiers used to perform operations with the electrode signals, may also perform the function of the sensing circuitry 1204. Combining the functions of sensing circuitry 1204 and noise reduction circuitry 1203 may be useful to minimize the necessary componentry and lower the power requirements of the system.

In the illustrative configuration shown in FIG. 7, the detection circuitry 1202 is coupled to, or otherwise incorporates, noise reduction circuitry 1203. The noise reduction circuitry 1203 operates to improve the SNR of sensed cardiac signals by removing noise content of the sensed cardiac signals introduced from various sources. Typical types of cardiac signal noise includes electrical noise and noise produced from skeletal muscles, for example. A number of methodologies for improving the SNR of sensed cardiac signals in the presence of skeletal muscular induced noise, including signal separation techniques incorporating combinations of electrodes and multi-element electrodes, are described hereinbelow.

Detection circuitry 1202 may include a signal processor that coordinates analysis of the sensed cardiac signals and/or other sensor inputs to detect cardiac arrhythmias, such as, in particular, tachyarrhythmia. Rate based and/or morphological discrimination algorithms may be implemented by the signal processor of the detection circuitry 1202 to detect and verify the presence and severity of an arrhythmic episode. Examples of arrhythmia detection and discrimination circuitry, structures, and techniques, are disclosed in commonly owned U.S. Pat. Nos. 5,301,677, 6,438,410, and 6,708,058, which are hereby incorporated herein by reference.

The detection circuitry 1202 communicates cardiac signal information to the control system 1205. Memory circuitry 1209 of the control system 1205 contains parameters for operating in various monitoring, pacing, and, if applicable, defibrillation modes, and stores data indicative of cardiac signals received by the detection circuitry 1202. The memory circuitry 1209 may also be configured to store historical EGM and therapy data, which may be used for various purposes and transmitted to an external receiving device as needed or desired.

In certain configurations, the PIMD may include diagnostics circuitry 1210. The diagnostics circuitry 1210 typically receives input signals from the detection circuitry 1202 and the sensing circuitry 1204. The diagnostics circuitry 1210 provides diagnostics data to the control system 1205, it being understood that the control system 1205 may incorporate all or part of the diagnostics circuitry 1210 or its functionality. The control system 1205 may store and use information provided by the diagnostics circuitry 1210 for a variety of diagnostics purposes. This diagnostic information may be stored, for example, subsequent to a triggering event or at predetermined intervals, and may include system diagnostics, such as power source status, therapy delivery history, and/or patient diagnostics. The diagnostic information may take the form of electrical signals or other sensor data acquired immediately prior to therapy delivery.

According to a configuration that provides cardioversion and defibrillation therapies, the control system 1205 processes cardiac signal data received from the detection circuitry 1202 and initiates appropriate tachyarrhythmia therapies to terminate cardiac arrhythmic episodes and return the heart to normal sinus rhythm. The control system 1205 is coupled to shock therapy circuitry 1216. The shock therapy circuitry 1216 is coupled to the electrode(s) 1214 and the can or indifferent electrode 1207 of the PIMD housing.

Upon command, the shock therapy circuitry 1216 delivers cardioversion and defibrillation stimulation energy to the heart in accordance with a selected cardioversion or defibrillation therapy. In a less sophisticated configuration, the shock therapy circuitry 1216 is controlled to deliver defibrillation therapies, in contrast to a configuration that provides for delivery of both cardioversion and defibrillation therapies. Examples of PIMD high energy delivery circuitry, structures and functionality, aspects of which may be incorporated in a PIMD of a type that may benefit from aspects of the present invention are disclosed in commonly owned U.S. Pat. Nos. 5,372,606; 5,411,525; 5,468,254; and 5,634,938, which are hereby incorporated herein by reference.

Arrhythmic episodes may also be detected and verified by morphology-based analysis of sensed cardiac signals as is known in the art. Tiered or parallel arrhythmia discrimination algorithms may also be implemented using both rate-based and morphologic-based approaches. Further, a rate and pattern-based arrhythmia detection and discrimination approach may be employed to detect and/or verify arrhythmic episodes, such as the approach disclosed in U.S. Pat. Nos. 6,487,443; 6,259,947; 6,141,581; 5,855,593; and 5,545,186, which are hereby incorporated herein by reference.

As is shown in FIG. 7, the PIMD includes pacing therapy circuitry 1230 that is coupled to the control system 1205 and the electrode(s) 1214 and can/indifferent electrodes 1207. Upon command, the pacing therapy circuitry 1230 delivers pacing pulses to the heart in accordance with a selected pacing therapy.

Control signals, developed in accordance with a pacing regimen by pacemaker circuitry within the control system 1205, are initiated and transmitted to the pacing therapy circuitry 1230 where pacing pulses are generated. A pacing regimen, such as those discussed and incorporated herein, may be modified by the control system 1205. In one particular application, a phrenic nerve stimulation avoidance methodology of the present invention may be implemented to enhance capture detection and/or capture threshold determinations, such as by selecting an optimal vector for sensing an evoked response resulting from application of a capture pacing stimulus that does not cause phrenic nerve stimulation.

The PIMD shown in FIG. 7 may be configured to receive signals from one or more physiologic and/or non-physiologic sensors. Depending on the type of sensor employed, signals generated by the sensors may be communicated to transducer circuitry coupled directly to the detection circuitry 1202 or indirectly via the sensing circuitry 1204. It is noted that certain sensors may transmit sense data to the control system 1205 without processing by the detection circuitry 1202.

Communications circuitry 1218 is coupled to the microprocessor 1206 of the control system 1205. The communications circuitry 1218 allows the PIMD to communicate with one or more receiving devices or systems situated external to the PIMD. By way of example, the PIMD may communicate with a patient-worn, portable or bedside communication system via the communications circuitry 1218. In one configuration, one or more physiologic or non-physiologic sensors (subcutaneous, cutaneous, or external of patient) may be equipped with a short-range wireless communication interface, such as an interface conforming to a known communications standard, such as Bluetooth or IEEE 802 standards.

Data acquired by such sensors may be communicated to the PIMD via the communications circuitry 1218. It is noted that physiologic or non-physiologic sensors equipped with wireless transmitters or transceivers may communicate with a receiving system external of the patient.

The communications circuitry 1218 allows the PIMD to communicate with an external programmer and/or advanced patient management device. In one configuration, the communications circuitry 1218 and the programmer unit (not shown) use a wire loop antenna and a radio frequency telemetric link, as is known in the art, to receive and transmit signals and data between the programmer unit and communications circuitry 1218. In this manner, programming commands and data are transferred between the PIMD and the programmer unit during and after implant. Using a programmer, a physician is able to set or modify various parameters used by the PIMD. For example, a physician may set or modify parameters affecting monitoring, detection, pacing, and defibrillation functions of the PIMD, including pacing and cardioversion/defibrillation therapy modes. The programmer and/or advanced patient management device may include a signal processor to process signals and implement phrenic nerve stimulation reduction algorithms and processes in accordance with the present invention.

Typically, the PIMD is encased and hermetically sealed in a housing suitable for implanting in a human body as is known in the art. Power to the PIMD is supplied by an electrochemical power source 1220 housed within the PIMD. In one configuration, the power source 1220 includes a rechargeable battery. According to this configuration, charging circuitry is coupled to the power source 1220 to facilitate repeated non-invasive charging of the power source 1220. The communications circuitry 1218, or separate receiver circuitry, is configured to receive RF energy transmitted by an external RF energy transmitter. The PIMD may, in addition to a rechargeable power source, include a non-rechargeable battery. It is understood that a rechargeable power source need not be used, in which case a long-life non-rechargeable battery is employed.

The detection circuitry 1202, which is coupled to a microprocessor 1206, may be configured to incorporate, or communicate with, specialized circuitry for processing sensed signals in manners particularly useful in a cardiac sensing and/or stimulation device that includes phrenic nerve stimulation reduction. As is shown by way of example in FIG. 7, the detection circuitry 1202 may receive information from multiple physiologic and non-physiologic sensors.

Various PIMD embodiments described herein may be used in connection with advanced patient management. Methods, structures, and/or techniques described herein, which may be adapted to provide for remote patient/device monitoring, diagnosis, therapy, or other APM related methodologies, may incorporate features of one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A medical device, comprising:
   a plurality of electrodes electrically coupled to a heart;
   a pulse delivery circuit configured to deliver a plurality of pacing pulses to a heart using the plurality of electrodes;
   a transthoracic impedance sensor configured to sense a transthoracic impedance signal; and
   a control circuit coupled to the sensing circuit and the transthoracic impedance sensor, the control circuit configured to determine the presence of phrenic nerve stimulation resulting from the pacing pulses based on deviations in the transthoracic impedance signal corresponding to delivery of the plurality of pacing pulses and verify the presence of phrenic nerve stimulation resulting from the pacing pulses based on an additional deviation in the transthoracic impedance signal corresponding to an additional pulse delivered during a cardiac refractory period of the heart by the pulse delivery circuit using the plurality of electrodes.

2. The device of claim 1, wherein the control circuit is configured to provide pacing pulse parameters to the pulse delivery circuit that reduce phrenic nerve stimulation while maintaining cardiac capture.

3. The device of claim 1, wherein the control circuit is configured to determine one or more pacing pulse parameters that reduce phrenic nerve stimulation while maintaining cardiac capture.

4. The device of claim 1, wherein a signal processor is provided in a patient-external device or system, the signal processor and the control circuit coupled to respective communication devices to facilitate wireless communication between the signal processor and the control circuit.

5. The device of claim 1, wherein a signal processor is provided in a network server system, the signal processor and the control circuit coupled to respective communication devices to facilitate wireless communication between the signal processor and the control circuit.

6. The device of claim 1, wherein the control circuit is configured to select a pacing vector that reduces the phrenic nerve stimulation while maintaining cardiac capture.

7. The device of claim 1, wherein the deviations in the transthoracic impedance signal correspond to delivery of the plurality of pacing pulses when a delivery frequency of the pacing pulses corresponds to a frequency of the deviations in the transthoracic impedance signal.

8. The device of claim 1, further comprising a band pass filter centered at a frequency corresponding to a pacing rate of the plurality of pacing pulses, the band pass filter configured to filter the transthoracic impedance signal.

9. The device of claim 1, wherein the deviations in the transthoracic impedance signal correspond to delivery of the plurality of pacing pulses when each of the deviations are respectively sensed in one of a plurality of time windows, each of the time windows respectively opening in response to delivery of one of the plurality of pacing pulses and remaining open for up to about 500 milliseconds.

10. The device of claim 1, wherein the deviations in the transthoracic impedance signal correspond to delivery of the plurality of pacing pulses when the deviations temporally correspond to delivery of the plurality of pacing pulses.

11. The device of claim 1, wherein an extent of the deviations in the transthoracic impedance signal are determined relative to a predetermined threshold.

12. A medical device, comprising:
   means for sensing an electrophysiologic signal from a heart;
   means for delivering a plurality of pacing pulses to the heart;
   means for detecting a cardiac signal following the pacing pulse;

means for sensing a transthoracic impedance signal;

means for detecting a phrenic nerve stimulation from the pacing pulses using a plurality of deviations in the transthoracic impedance signal corresponding to delivery of the plurality of pacing pulses; and means for verifying the presence of phrenic nerve stimulation resulting from the pacing pulses based on an additional deviation in the transthoracic impedance signal corresponding to an additional pulse delivered during a cardiac refractory period.

13. The device of claim 12, comprising means for determining a temporal relationship between the transthoracic impedance signal and the electrophysiologic signal.

14. The device of claim 12, comprising means for selecting a pacing vector that effects cardiac capture and reduces the phrenic nerve stimulation.

15. The device of claim 12, comprising means for selecting a pacing voltage that effects cardiac capture and reduces the phrenic nerve stimulation.

16. The device of claim 12, comprising means for selecting a pacing pulse width that effects cardiac capture and reduces the phrenic nerve stimulation.

17. The device of claim 12, comprising means for transmitting information associated with the sensed electrophysiologic signals and the sensed transthoracic impedance signal to a patient-external device.

18. The device of claim 12, wherein the plurality of deviations in the transthoracic impedance signal correspond to delivery of the plurality of pacing pulses when a delivery frequency of the pacing pulses corresponds to a frequency of the plurality of deviations in the transthoracic impedance signal.

19. The device of claim 12, wherein the plurality of deviations in the transthoracic impedance signal correspond to delivery of the plurality of pacing pulses when the plurality of deviations temporally correspond to delivery of the plurality of pacing pulses.

* * * * *